(12) United States Patent
Bauer et al.

(10) Patent No.: US 10,876,965 B2
(45) Date of Patent: *Dec. 29, 2020

(54) APPARATUS AND METHOD FOR ANALYZING A MATERIAL

(71) Applicant: DiaMonTech GmbH, Berlin (DE)

(72) Inventors: Alexander Bauer, Oberursel (DE); Otto Hertzberg, Frankfurt am Main (DE); Thorsten Lubinski, Berlin (DE)

(73) Assignee: DiaMonTech AG, Berlin (DE)

( * ) Notice: Subject to any disclaimer, the term of this patent is extended or adjusted under 35 U.S.C. 154(b) by 27 days.

This patent is subject to a terminal disclaimer.

(21) Appl. No.: 15/781,176

(22) PCT Filed: Dec. 9, 2015

(86) PCT No.: PCT/DE2015/200532
§ 371 (c)(1),
(2) Date: Jun. 4, 2018

(87) PCT Pub. No.: WO2017/097276
PCT Pub. Date: Jun. 15, 2017

(65) Prior Publication Data
US 2019/0302019 A1    Oct. 3, 2019

(51) Int. Cl.
*G01N 21/552* (2014.01)
*G01N 21/63* (2006.01)
(Continued)

(52) U.S. Cl.
CPC ......... *G01N 21/552* (2013.01); *A61B 5/0004* (2013.01); *A61B 5/1455* (2013.01);
(Continued)

(58) Field of Classification Search
CPC ............... G01N 21/552; G01N 21/171; G01N 21/1717; G01N 21/636; G01N 33/49;
(Continued)

(56) References Cited

U.S. PATENT DOCUMENTS 4,529,319 A    7/1985   Muller
4,790,664 A    12/1988  Saito et al.
(Continued)

FOREIGN PATENT DOCUMENTS

AU    2008325237 B2    5/2014
CN    1555242 A       12/2004
(Continued)

OTHER PUBLICATIONS

International Searching Authority—EPO, International Search Report, PCT/DE2015/200532; dated May 17, 2016. 3 pages.
(Continued)

*Primary Examiner* — Jamil Ahmed
(74) *Attorney, Agent, or Firm* — Sunstein LLP

(57) ABSTRACT

The invention relates, inter alia, to an apparatus (10) for analyzing a material (101), comprising an excitation emission device (100) for generating at least one electromagnetic excitation beam (SA), in particular an exciting light beam, having at least one excitation wavelength, further comprising a detection device (106) for detecting a reaction signal (SR), and a device (107) for analyzing the material on the basis of the detected reaction signal (SR).

17 Claims, 5 Drawing Sheets

(51) Int. Cl.
*A61B 5/1455* (2006.01)
*A61B 5/00* (2006.01)
*G01N 21/17* (2006.01)
*A61B 5/145* (2006.01)
*A61B 5/1495* (2006.01)
*G01N 33/49* (2006.01)

(52) U.S. Cl.
CPC ......... *A61B 5/4839* (2013.01); *G01N 21/171* (2013.01); *G01N 21/1717* (2013.01); *G01N 21/636* (2013.01); *A61B 5/1451* (2013.01); *A61B 5/1495* (2013.01); *A61B 5/14532* (2013.01); *A61B 2560/0238* (2013.01); *G01N 33/49* (2013.01); *G01N 2021/1712* (2013.01); *G01N 2021/1725* (2013.01); *G01N 2201/06113* (2013.01)

(58) Field of Classification Search
CPC ... G01N 2021/1712; G01N 2021/1725; G01N 2201/06113; A61B 5/0004; A61B 5/1455; A61B 5/4839; A61B 5/1451; A61B 5/14532; A61B 5/1495; A61B 2560/0238
See application file for complete search history.

(56) References Cited

U.S. PATENT DOCUMENTS

| | | |
|---|---|---|
| 4,952,027 A | 8/1990 | Saito et al. |
| 4,968,144 A | 11/1990 | Thomas et al. |
| 5,136,172 A | 8/1992 | Nakata et al. |
| 5,370,114 A | 12/1994 | Wong et al. |
| 5,513,006 A | 4/1996 | Schulz et al. |
| 5,574,283 A | 11/1996 | Quintana |
| 6,332,868 B1 | 12/2001 | Sato et al. |
| 6,421,548 B1 | 7/2002 | Berman et al. |
| 6,424,851 B1 | 7/2002 | Berman et al. |
| 6,484,044 B1 * | 11/2002 | Lilienfeld-Toal .... A61B 5/0095 600/310 |
| 7,133,710 B2 | 11/2006 | Acosta et al. |
| 7,215,982 B2 | 5/2007 | Oshima et al. |
| 7,262,836 B2 | 8/2007 | Uchida et al. |
| 7,438,855 B2 | 10/2008 | Sota et al. |
| 7,576,862 B2 | 8/2009 | Cromwell et al. |
| 9,554,735 B2 | 1/2017 | Rebec et al. |
| 9,784,620 B2 | 10/2017 | Witinski et al. |
| 9,833,179 B2 | 12/2017 | Ikeda |
| 9,915,608 B2 | 3/2018 | Schultz et al. |
| 2006/0281982 A1 | 12/2006 | Grata et al. |
| 2009/0247843 A1 | 10/2009 | Xu |
| 2010/0220952 A1* | 9/2010 | Smith ................... H01S 5/0683 385/14 |
| 2013/0286397 A1* | 10/2013 | Witinski ................ G01J 3/42 356/409 |
| 2015/0192461 A1 | 7/2015 | Chen |
| 2017/0146455 A1* | 5/2017 | Mantele ............... A61B 5/1495 |
| 2018/0348053 A1 | 12/2018 | Koide |

FOREIGN PATENT DOCUMENTS

| | | |
|---|---|---|
| CN | 1638690 A | 7/2005 |
| CN | 101263388 A | 9/2008 |
| CN | 100511623 C | 7/2009 |
| CN | 102226752 A | 10/2011 |
| CN | 102033048 B | 5/2012 |
| CN | 104541193 A | 4/2015 |
| DE | 39 37 905 C1 | 5/1991 |
| DE | 4446390 | 7/1996 |
| DE | 102005048807 | 11/2006 |
| DE | 102014108424 | 6/2015 |
| DE | 102014108424 B3 * | 6/2015 ......... A61B 5/14546 |
| EP | 0 427 943 A1 | 5/1991 |
| EP | 1 048 265 A1 | 11/2000 |
| HU | 225 660 B1 | 5/2007 |
| JP | S6363945 A | 3/1988 |
| JP | H03-156362 | 7/1991 |
| JP | 2846079 B2 | 10/1998 |
| JP | 2000-204904 A | 7/2000 |
| JP | 2000-232970 A | 8/2000 |
| JP | 2005-127748 A | 5/2005 |
| JP | 2005-535411 A | 11/2005 |
| JP | 2006-242816 A | 9/2006 |
| JP | 2007-242747 A | 9/2007 |
| JP | 4052461 B2 | 2/2008 |
| JP | 2008-107098 A | 5/2008 |
| JP | 2008-125542 A | 6/2008 |
| JP | 2008-543437 | 12/2008 |
| JP | 2009-219800 | 10/2009 |
| JP | 2012-070907 | 4/2012 |
| JP | 2012-119409 A | 6/2012 |
| JP | 4963482 B2 | 6/2012 |
| JP | 5628008 B2 | 11/2014 |
| JP | 6201315 B2 | 9/2017 |
| JP | 6387610 B2 | 9/2018 |
| NO | 300346 B1 | 5/1997 |
| RU | 135139 U1 | 11/2013 |
| WO | WO 95/31133 | 11/1995 |
| WO | WO 96/31765 | 10/1996 |
| WO | WO 00/21437 | 4/2000 |
| WO | WO 03/100393 A1 | 12/2003 |
| WO | WO 2004/016171 A1 | 2/2004 |

OTHER PUBLICATIONS

International Bureau, International Preliminary Report on Patentability, International Application No. PCT/DE2015/200532, dated Jan. 9, 2018, 8 pages [English Translation].
European Patent Office, International Search Report and Written Opinion of the International Searching Authority, Application No. PCT/EP2015/063470, dated Sep. 18, 2015, 15 pages.
European Patent Office, International Preliminary Report on Patentability, Application No. PCT/EP2016/080046, dated Jan. 22, 2018, 8 pages.
R.H. Farahi et al. *Pump probe photothermal spectroscopy using quantum cascade lasers*, Journal of Physics D: Applied Physics, Vo. 45, No. 12, Mar. 6, 2012, 7 pages.
Guo et al., *Noninvasive glucose detection in human skin using wavelength modulated differential laser photothermal radiometry*, Biomedical Optics Express, vol. 3, No. 11, Nov. 1, 2012, 10 pages.
George, *Fibre Optic position sensitive detection of photothermal deflection*, Applied Physics B, vol. 77, 2003, pp. 77-80.
Fujinami et al., *Highly sensitive detection of molecules at the liquid/liquid interface using total internal reflection-optical beam deflection based on photothermal spectroscopy*, Review of Scientific Instruments, vol. 74, No. 1, Jan. 2003, pp. 352-354.
Kawazumi et al., *Development of an interfacial thermal lens technique: monitoring the dissolving process of amphiphilic molecules at the hexane-water interface*, Chemical Physics Letters vol. 282, Jan. 9, 2998, pp. 159-163.
Naoki Wadamori et al., *Determination of Measurable Depth Based on Optical Modulation Frequency by Photoacoustic Spectroscopy*, Transactions of Japanese Society for Medical and Biological Engineering, vol. 49, No. 1 (2011), pp. 220-225 (with English abstract).
Naoki Wadamori et al., *Determination of Measurable Depth Based on Optical Modulation Frequency by Photoacoustic Spectroscopy*, Transactions of Japanese Society for Medical and Biological Engineering, vol. 49, No. 1 (2011), pp. 220-225 (with English translation).

* cited by examiner

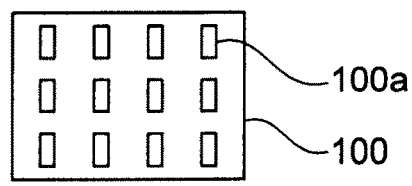
Fig. 2
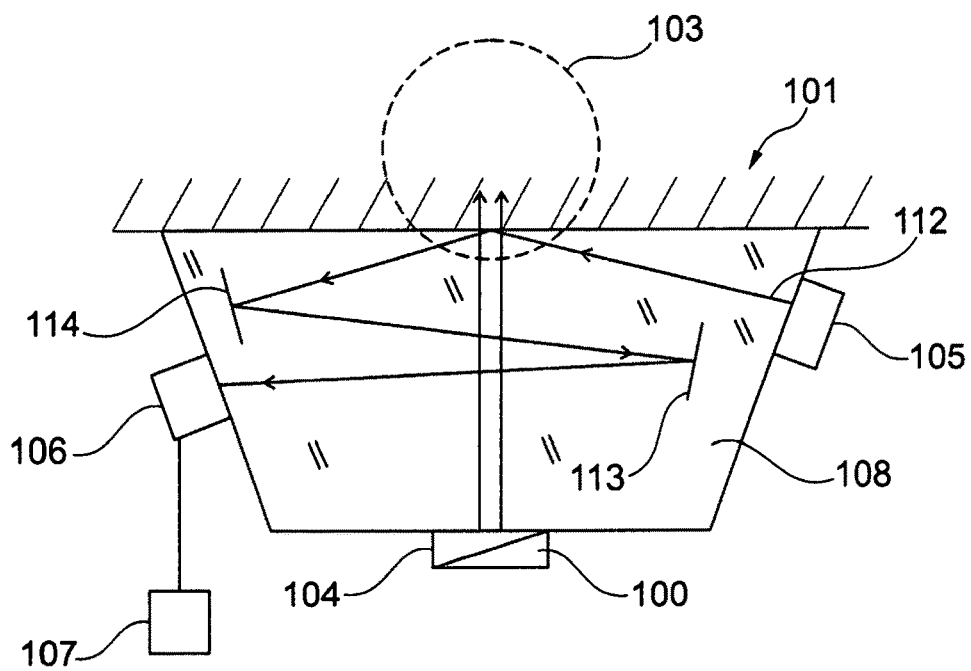
Fig. 3
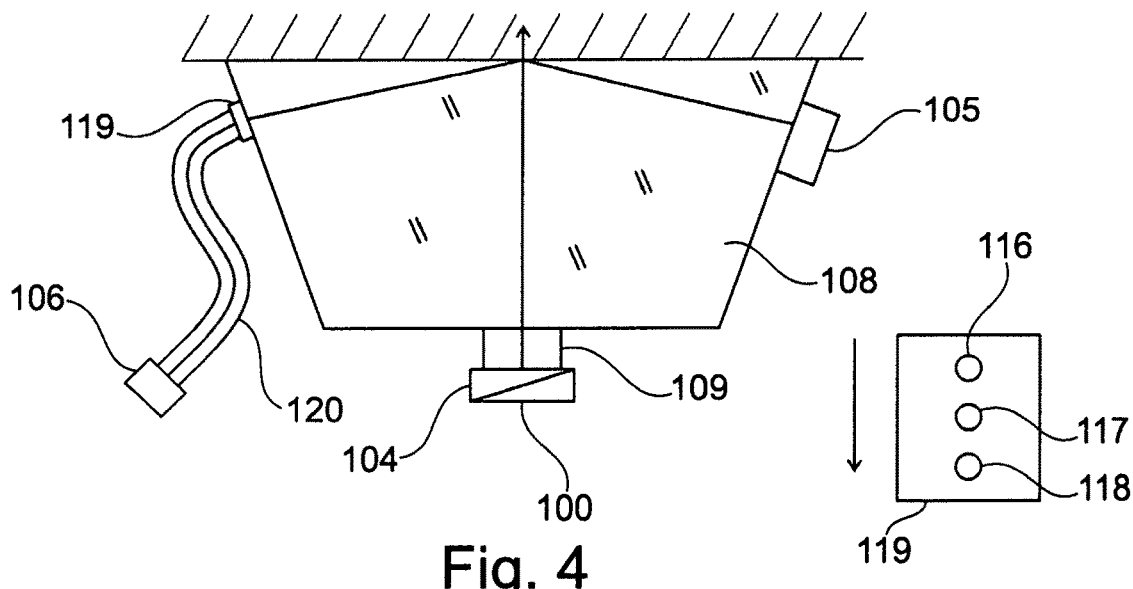
Fig. 4
Fig. 5

APPARATUS AND METHOD FOR ANALYZING A MATERIAL

CROSS-REFERENCE TO RELATED APPLICATIONS

This Application is a U.S. national stage entry under 35 USC § 371 of Patent Cooperation Treaty Application PCT/DE2015/200532, filed Dec. 9, 2015, which is incorporated herein by reference in its entirety.

TECHNICAL FIELD

The present intellectual property right relates to a device and a method for analyzing a material. The device described here and the procedure described here can be used for example for the analysis of animal or human tissue, in one embodiment for the measuring of glucose or blood sugar.

BACKGROUND

Known methods for analysing a material, in particular for the measurement of blood sugar are described in the following publications, for example:
Guo et al.: "Noninvasive glucose detection in human skin-using wavelength modulated differential laser photothermal radiometry", Biomedical Optics Express, Vol, 3, 2012, No. 11,
Uemura et al.: "Non-invasive blood glucose measurement by Fourier transform infrared spectroscopic analysis through the mucous membrane of the lip: application of a chalcogenide optical fiber System", Front Med Biol Eng. 1999; 9(2): 137-153,
Farahi et al.: "Pump probe photothermal spectroscopy using quantum cascade lasers", J. Phys. D. Appl. Phys. 2012 and
M. Fujinami et al.: "Highly sensitive detection of molecules at the liquid/liquid interface using total internal reflection-optical beam deflection based on photothermal spectroscopy", Rev. Sei. Instrum., Vol. 74, Number 1 (2003).
(1) von Lilienfeld-Toal, H. Weidenmüller, M. Xhelaj, A. Mäntele, W. A Novel Approach to Non-Invasive Glucose Measurement by Mid-Infrared Spectroscopy: The Combination of Quantum Cascade Lasers (QCL) and Photoacoustic Detection Vibrational Spectroscopy, 38:209-215, 2005.
(2) Pleitez, M. von Lilienfeld-Toal, H. Mäntele W. Infrared spectroscopic analysis of human interstitial fluid in vitro and in vivo using FT-IR spectroscopy and pulsed quantum cascade lasers (QCL): Establishing a new approach to non-invasive glucose measurement Spectrochimica acta. Part A, Molecular and biomolecular spectroscopy, 85:61-65, 2012
(3) Pleitez, M. et al. In Vivo Noninvasive Monitoring of Glucose Concentration in Human Epidermis by Mid-Infrared Pulsed Photoacoustic Spectroscopy Analytical Chemistry, 85: 1013-1020, 2013
(4) Pleitez, M. Lieblein, T. Bauer, A. Hertzberg, 0. von Lilienfeld-Toal, H. Mäntele, W Windowless ultrasound photoacoustic cell for in vivo mid-IR spectroscopy of human epidermis: Low interference by changes of air pressure, temperature, and humidity caused by skin contact opens the possibility for a non-invasive monitoring of glucose in the interstitial fluid Review of Scientific Instruments 84, 2013
(5) M. A. Pleitez Rafael, O. Hertzberg, A. Bauer, M. Seeger, T. Lieblein, H. von Lilienfeld-Toal, and W. Mäntele. Photo-thermal deflectometry enhanced by total internal reflection enables non-invasive glucose monitoring in human epidermis. The Analyst, November 2014.

SUMMARY OF THE EMBODIMENTS

The object if the invention is to specify a device with which a material, in particular an animal or human tissue or a component or ingredient of the tissue, can be analysed particularly simply and cost-effectively.

This object is achieved by, inter alia, a device having the features as defined in claim 1. Embodiments of the device are specified in dependent claims.

Reference is made to the German patent DE 10 2014 108 424 B3, the content of which is referred to specifically, and the content of which this application extends; by this explicit reference made here, the full contents of German patent DE 10 2014 108 424 B3 is therefore also to be regarded as part of the disclosure of this application ("incorporation by reference" for all details of that disclosure). In particular, this reference relates to all the features given in the patent claims as granted. In addition, the reference relates in particular to details of the excitation light beam mentioned there, for example, to the numerical values of the pulse frequencies and wavelengths (wavelength ranges) cited there, and also to the details relating to the measurement of glucose content in the interstitial fluid.

In addition to the subject matter of the claims and exemplary embodiments which are directly and explicitly mentioned at the time of filing, the present PCT property rights application also relates to other aspects, which are listed at the end of the present description. These aspects can be combined, either individually or in groups, with features of the claims cited at the time of filing. These aspects, whether taken alone or combined with each other or with the subject matter of the claims, represent stand-alone inventions. The applicant reserves the right to make these inventions the subject matter of claims at a later date. This can be done in the context of this application or else in the context of subsequent divisional applications, continuation applications (in the USA), continuation-in-part applications (in the USA) or subsequent applications claiming the priority of this application.

In the following, however, the subject matter of the claims mentioned at the time of filing will be discussed first.

A device for analysing a material is provided, with an excitation transmission device for generating at least one electromagnetic excitation beam, in particular an excitation light beam with at least one excitation wavelength, a detection device for detecting a response signal and a device for analysing the material on the basis of the detected response signal.

A major advantage of this device is the fact that it can be used to analyse a material in a very simple and reliable way.

The term light is understood here to mean electromagnetic waves or electromagnetic radiation in the visible range, in the near and far infrared range and in the UV range.

In an exemplary embodiment of the device it is provided that the excitation transmission device is a radiation source, in one embodiment a monochromatic, in particular polarised radiation source or light source, more particularly a laser light source,
the device has an optical medium, which is in direct contact with the material, in particular with a first region of the surface of the material,
wherein the excitation transmission device is preferably arranged in such a way that the emitted excitation beam penetrates the optical medium and exits the same again at a predetermined point on the surface of the optical medium, and the device comprises a system for emitting a measuring beam, in particular a measuring light beam, which is arranged in such a way that the emitted measuring beam penetrates into the optical medium and wherein in operation the measuring beam and the excitation beam preferably overlap at an interface of the optical medium and the surface of the material at which the measuring beam is reflected, and the detection device is a device for receiving the reflected measuring beam which forms the response signal, and/or for directly or indirectly detecting a deflection of the reflected measuring beam.

Preferably, the device has an optical medium which is in direct contact with the material, in particular with a first region of the surface of the material, in one embodiment the skin of a human being, wherein for detecting a response signal the detection device detects a parameter change of the optical medium, in particular in a region adjacent to the first region, as a result of the response signal, in particular a deformation and/or density change of the optical medium as a result of a local, time-dependent heating. The optical medium may consist of a material which is optically transparent or transparent to infrared radiation or ultraviolet radiation, in general to the excitation beam and the measuring beam, such as glass, crystal, zinc sulphide (ZnS), zinc selenide (ZnSe), germanium (Ge), silicon (Si) and diamond or a transparent plastic, in one embodiment a polyethylene. A local heating in response to a transport or transfer of heat from the material to be analysed or from a substance of the material into the optical medium leads to a change therein, for example, a material deformation or thermal stresses or local changes in refractive index, which are detectable.

The material can in one embodiment be the tissue of a living organism, in particular a human being, wherein the material surface can be the skin. Substances in the tissue can then be analysed or measured.

It can also be provided that the detection device has a piezo-element connected to the optical medium or integrated into it, as a detector for detecting a stress, deformation and/or density change.

It can also be provided that the detection device has at least one temperature sensor as a detector for detecting the response signal. This can be arranged directly on the optical medium or in its surroundings, depending on the measuring principle.

Preferably, the device has a system for intensity modulation of the excitation light beam.

The detection device is preferably suitable for detecting a time-dependent response signal as a function of the wavelength of the excitation light and/or the intensity modulation of the excitation light.

It can also be provided that the excitation transmission device radiates at least one electromagnetic excitation beam into a volume of material, which is underneath a first region of the surface of the material.

Particularly preferably the excitation transmission device comprises two or more transmission elements, in particular in the form of a one-, two- or multi-dimensional transmission element array. This can therefore be implemented as a surface array of transmission elements, or else as a transmission element strip (in one embodiment semiconductor laser arrays or QCL arrays, wherein QCL stands for quantum cascade laser).

It can also be provided that the two or more transmission elements each generate their own electromagnetic excitation beam and radiate this into the volume underneath the first region. The different excitation beams can also be emitted successively, or else at least partially at the same time. The different transmission elements can also be operated with different modulation frequencies at the same time.

The wavelengths of the electromagnetic excitation beams of the two or more transmission elements are preferably different. The wavelengths are preferably chosen in such a way that a substance to be detected in the material to be analysed absorbs radiation of these wavelengths particularly well. Additionally or alternatively, wavelengths or wavelength ranges can also be selected, which the substance to be detected does not absorb, but which are absorbed by other substances (so-called tolerant wavelengths), to distinguish the substance to be analysed from other substances.

In one embodiment the excitation transmission device comprises two or more lasers, in particular in the form of a one- or two-dimensional laser array, wherein a plurality of rows of laser elements can be staggered and arranged offset one behind another in order to save space, in one embodiment in the form of a laser strip and/or two or more light-emitting diodes, in particular in the form of a one- or two-dimensional diode array, in a depth-staggered manner and offset relative to one another, in one embodiment of a two-dimensional array or a strip. The output beams of the arrays can either have individual beam axes, close together or in parallel, for each beam element, or can have a same beam axis, by means of already integrated sets of optics.

Regarding the structure of the device, it can be provided that the excitation transmission device is directly or indirectly—preferably by means of an adjustment device—mechanically fixedly connected to an optical medium, which is in direct contact with the material, in particular with the first region of the surface of the material. Therefore, the excitation transmission device can be aligned and fixed relative to the optical medium as early as the manufacturing stage, or at least before deployment.

For the purpose of mounting and/or alignment or adjustment of an excitation transmission device and/or elements of a detection device, the optical medium can have at least one built-in elevation and/or indentation, such as a bridge, a shoulder, a half-sphere mounted thereon, a mounted block, a cone or a drilled hole, a groove, a hollow or other recess, in or on which the above-mentioned elements (the excitation transmission device and/or elements of a detection device) can be placed, rested on or to which they can be aligned or fixed. It is also possible that aligned matching surfaces be formed on the optical medium by machining or in a casting process.

With regard to the device for intensity modulation it can be provided that it comprises an electrical or electro-mechanical modulation device, which is electrically connected to the excitation transmission device and in particular, electrically controls the same, or is formed by such a device. The modulation device can generate an intensity modulation of the excitation beam, in one embodiment a periodic intensity modulation, also for example in the form of rectangular pulses, a sawtooth function or a sine-wave function or other periodic function.

Alternatively or additionally, the device for intensity modulation can comprise at least one controlled mirror arranged in the beam path, by the control of which the intensity of the excitation beam can be modulated by deflection.

Alternatively or additionally, the device for intensity modulation can comprise at least one layer, which is arranged in the beam path and is controllable with respect to its transparency, or can be formed by such a layer. Therefore, the modulation element can be designed in the form of a transmission element which is controlled with respect to its transmission. The modulation element can generate a plurality of spatially separated light beams from one light beam. It can also be provided in one embodiment that the surface of a sample can be scanned with the modulation element. In one embodiment, the modulation element can be controlled together with the array of light sources/laser sources.

A device for emitting a measuring beam, in particular a measuring light beam, is in one embodiment provided for emitting the measuring beam into the particular area of an optical medium, which is in contact with the first region of the surface of the material.

The device for emitting a measuring beam and the detection device are aligned to each other in one embodiment in such a way that the detection device detects the measuring beam as the time-dependent response signal, after this beam has been reflected at least once at the interface of the optical medium that is in contact with the material, in particular with the first region of the surface of the material.

With a view to ease of assembly, it is advantageous if the device for emitting a measuring beam and/or the detection device and/or the excitation transmission device are directly fixedly mechanically connected to the optical medium and/or are coupled to the same by means of one or more fibre-optic cables.

Embodiments are also possible, in which the optical medium directly supports an imaging optics and/or an imaging optics is integrated into the optical medium.

In addition, embodiments are conceivable in which the surface of the optical medium has a plurality of partial faces inclined towards each other, at which the measuring beam, in particular the measuring light beam, is reflected multiple times.

Embodiments can also be provided, in which one or more mirror surfaces for reflection of the measuring beam, in particular the measuring light beam, are provided in or on the optical medium.

With a view to a compact design, it is conceivable that the excitation transmission device and/or the device for emitting the measuring beam and/or the detection device are directly attached to each other or to a common support. In one embodiment, the various devices can be fixed to the support by welding or gluing or by screws or a snap-in connection, wherein an adjustment facility can be provided, either during assembly or else at a later time, by means of an adjusting screw or other mechanical adjustment device. In particular, the device for emitting the measuring beam and/or the detection device should be, or capable of being, easily aligned with respect to each other. Therefore, it can be useful to attach these two devices directly to the optical medium. The device for emitting the measuring beam and/or the detection device, given suitable guidance of the measuring beam, can also be arranged next to each other on the same side of the optical medium and on a common support, in one embodiment attached to a common printed circuit board or a common semiconductor, or else implemented as a common integrated semiconductor device, in one embodiment as a common integrated semiconductor component. This support can then be adjusted as a unit relative to the optical medium, in a particular embodiment, even without further changing the relative position between the device for transmitting the measuring beam and/or the detection device.

The support is preferably formed by a printed circuit board, a metal plate or plastic plate or a housing or part of a housing of the device.

It can also be provided that the excitation transmission device comprises an integrated semiconductor device, which has one or more laser elements and at least one micro-optical component and preferably an additional modulation element. The above-mentioned elements can be manufactured, in one embodiment etched, jointly from one semiconductor blank or at least accommodated in a common housing.

It can also be provided that the modulation element has at least one element, in particular a mirror, which is movable relative to the rest of the semiconductor device and is controllable with respect to its position. This can be controlled by means of a MEMS device.

It can also be provided that the modulation element has a layer which is controllable in terms of its radiation permeability.

It can also be provided that the modulation element has an electronic control circuit for the modulation of the one or more laser elements. In one embodiment the modulation element can be constructed in such way that it varies the excitation beam in a time-dependent manner by interference, phase offset/path offset or a polarising filter device or other known modulation mechanisms.

The micro-optical component or components can be mirrors or lenses that are either integrated into the semiconductor component or made from it in a subtractive process, in particular by etching.

The described device for analysing a material can determine a measurement value of a material concentration, in one embodiment a glucose concentration. The device can have an interface to a device for displaying measurement values and their analysis, for example by means of a colour code for a user of the device, and/or to a dosing device for a substance which can be dispensed into the material, in particular the tissue or, more generally, the body of an organism. The device can also directly comprise such a dosing device. In this case, the device can also have a system for detecting or analysing the material surface, in one embodiment the skin surface or in another embodiment the ocular surface or iris of a living being, which enables the identification of a person or a living being based on a comparison with reference data and can therefore be used to ensure that appropriate reference values and/or calibration values are provided for the analysis of the material and the control of the dosing device. Determined characteristic values of the material surface, in one embodiment a fingerprint or the structure of an iris of the eye, can, in addition to identifying and authenticating a person, e. g. against a database, also be used for encrypting the communication of status values and controlling the dosing device which, encrypted or unencrypted, can in principle be originated from the database. In one embodiment the dosing device can be equipped with a sensor to determine a fill level of a substance to be dispensed, such as in one embodiment insulin and/or glucagon, and can have a device for transmitting the fill level to the device for material analysis and/or directly to the database.

In addition, the device can have an interface, in one embodiment a radio interface to the database, to which the measurement values can be sent and which can process the data. The database can be created in such a way that it processes and stores the data from a plurality of patients, that is, in one embodiment also the data from a plurality of similar devices for analysing a material, and in one embodiment it also controls individual dosing devices for dispensing substances. The database can also further process the measured data relating to the analysed material and determine derived analysis results, such as any trend in the values, first and second time derivatives, minima, maxima, standard deviations of material quantities or concentrations, blood sugar values or other physiological values of patients, compare them and derive signals from them, which in one embodiment also includes alarm signals. The fill level of the dosing device can also be detected and processed by the database in order to determine, in one embodiment, a temporal extent of the fill level or the need for refilling and to signal this directly to the patient's device or to a service facility. For this purpose, the database can be connected to a communication device in a service facility, in one embodiment in a hospital or a medical practice. For the purpose of sending data from and/or to a database, the device can in one embodiment be connected to a mobile device or a pager by means of a radio link, in one embodiment Bluetooth or WLAN or Wifi, or other transmission methods. The device can also be directly equipped with a WLAN interface and an internet client.

The subject matter also relates to a method for analysing a material, wherein in the method at least one electromagnetic excitation beam with at least one excitation wavelength is generated with an excitation transmission device by the successive operation or the at least partially simultaneous operation of a plurality of laser emitters of a laser light source, and a response signal is detected with a detection device and the material is analysed on the basis of the detected response signal. In the method, the thermal diffusivity in the material and the temporal evolution or waveform of the response signal can be used to characterize the nature of the material or a spatial distribution of a substance in the material or to characterize the depth at which the excitation beam is absorbed.

In one embodiment it can be provided that using different modulation frequencies of the excitation transmission device, response signals, in particular temporal response signal waveforms or patterns, can be successively determined and that a plurality of response signal waveforms or patterns at different modulation frequencies can be combined with each other and that, in particular, specific information for a depth range under the surface is obtained from this.

It can also be provided that response signal waveforms or patterns are determined at different modulation frequencies for different wavelengths of the excitation beam and from these, in particular specific information is obtained for each depth range under the surface. When using a plurality of modulation frequencies of the pump beam at the same time, it is possible, for example, to resolve the detected signal into its frequencies using an appropriate analysis method, for example a Fourier transformation; the FT would only filter out the signal that corresponds to the desired frequency.

It can also be provided that an optical medium is brought into direct contact with the material, in particular with a first region of the surface of the material, the emitted excitation beam is generated and, in particular, emitted with the excitation transmission device in such a way that it penetrates into the optical medium and exits it again at a predetermined point on the surface of the optical medium, that a measuring beam, in particular a measuring light beam, is generated with a device for emitting a measuring beam in such a way that this beam penetrates the optical medium and that in particular, in operation, the measuring beam and the excitation beam overlap at an interface of the optical medium and the surface of the material at which the measuring beam is reflected, and that a reflected measuring beam which forms the response signal is measured and/or the deflection of the reflected beam is directly or indirectly detected with the detection device.

One aspect of the method is the focussing of the measurement of the response signal on selected depth ranges underneath the (distance intervals from the) material surface. The thermal wavelength d has the greatest influence on the depth range measured with the method. It is defined as $d=\sqrt{(D/(\pi*f))}$, where D is the thermal diffusivity of the sample (here for example, skin) and f is the modulation frequency of the excitation beam. Literature on the thermal diffusivity of skin:

U. Werner, K. Giese, B. Sennhenn, K. Piamann, and K. Kölmel, "Measurement of the thermal diffusivity of human epidermis by studying thermal wave propagation," Phys. Med. Biol. 37(1), 21-35 (1992).

A. M. Stoll, Heat Transfer in Biotechnology, Vol 4 of Ad-vances in Heat Transfer, J. P. Hartnett and T. Irvin, eds. (New York, Academic, 1967), p 117.

In one embodiment, to eliminate response signals from the topmost layers of the material, changes in the measurements compared to previous measurements can be used, in case the measurements in the top layers change more or less slowly in comparison to other, deeper layers.

This can be the case in an embodiment in measurements on human skin, where the topmost layers of the skin undergo virtually no exchange with the lower layers and therefore physiological parameters change very little. The time derivative of measurements can also be applied to provide response signals to exclude the signals from the topmost layers of the skin. Thus the measurement, or at least the evaluation, can be limited to or focused on the interstitial fluid in the skin.

It can also be provided that depending on a material concentration identified in the material, a dosing device for dispensing a substance, in particular into a patient's body, is controlled and/or an acoustic and/or visual signal is output and/or a signal is output to a processing device via a wireless connection. In this case, in addition to a currently determined measurement a temporal development or evolution of the measurement values, a derivative of the measurement value, average values of the measurements, maxima, minima, a standard deviation and predefined thresholds for measurement values can be taken into account and combined with the current measurement value. In one embodiment, the processing device can be a database or connected to a database, which collects and processes data from a plurality of patients. The database can be either directly connected to a control system of the device or be remote from and connected to it via a communication interface.

To obtain increased security when operating a dosing device, in particular for insulin, it can be provided that this is operated locally or from a database under the control of a preset standard procedure with preselected quantity deliveries at times that are or can be specified, and that by means of the above-described device meaningful deviations from preset delivery values can be determined that are used for the correction and improvement of the control of the dosing device. In this way, even in the event of a failure of the device at least a normal or emergency operation of the dosing device is guaranteed.

BRIEF DESCRIPTION OF THE DRAWINGS

FIGS. 1 to 13 schematically show different elements of the device and its elements, in some cases in different embodiments. Specifically, FIG. 1 shows a device in accordance with an embodiment of the invention;

FIG. 2 shows an excitation transmission device in accordance with an embodiment of the invention;

FIG. 3 shows a device in accordance with an embodiment of the invention;

FIG. 4 shows a device in accordance with an embodiment of the invention;

FIG. 5 shows a connector body in accordance with an embodiment of the invention;

FIG. 6 shows a device in accordance with an embodiment of the invention;

FIG. 7 shows a device in accordance with an embodiment of the invention;

FIG. 8 shows a device in accordance with an embodiment of the invention;

FIG. 9 shows a modulation device in accordance with an embodiment of the invention;

FIG. 10 shows an excitation light source in accordance with an embodiment of the invention;

FIG. 11 shows an excitation light source in accordance with an embodiment of the invention;

FIG. 12 shows a device in accordance with an embodiment of the invention; and

FIG. 13 shows a graph of a wavelength range blocked by a filter in accordance with an embodiment of the invention.

DETAILED DESCRIPTION OF SPECIFIC EMBODIMENTS

Figure 1:
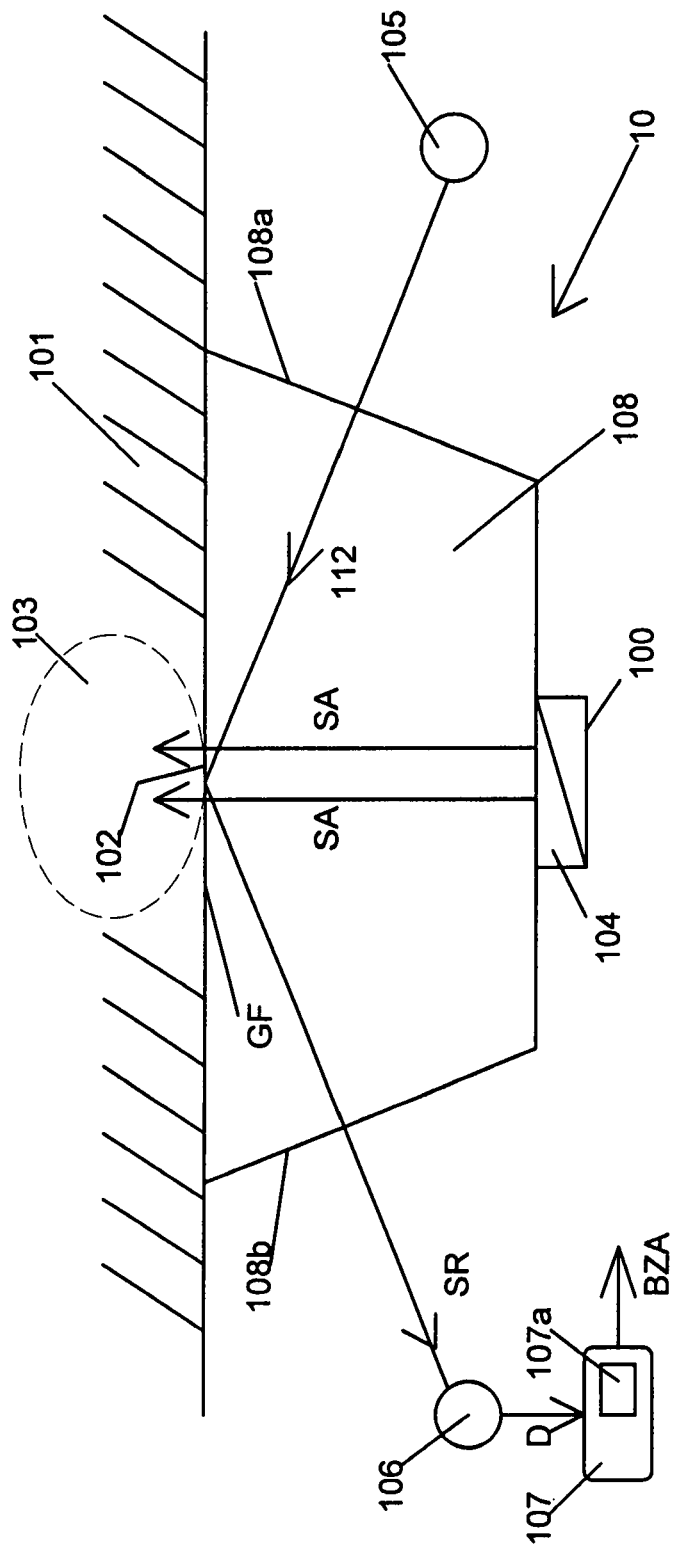

FIG. 1 shows an exemplary embodiment of a device 10 for analysing a material 101. The material 101 is preferably placed directly on an optical medium 108, which can be designed as an optically transparent crystal or glass body. The device for analysing the material 101 is used for example to measure the glucose or blood sugar content in a fluid, such as in one embodiment blood, and for producing a glucose or blood sugar level indication BZA.

The device comprises an excitation transmission device 100 for emitting one or more electromagnetic excitation beams SA, preferably in the form of excitation light beams with one or more excitation wavelengths, into a volume 103 which is located in the material 101 below a first region 102 of the surface of the material. The excitation transmission device 100 is also referred to in the following as "excitation light source" 100 for brevity. The excitation light source 100 can be a laser which is tunable with respect to its wavelength, in particular a tunable quantum cascade lasers; it is preferable, as will be explained below, to use a light source strip or a light source array with at least two single emitters, in particular semiconductor lasers, each of which emits a specified individual wavelength.

In addition, a device 104 for the intensity modulation of the excitation light beam or beams SA is provided, which is preferably formed by a modulation device for the excitation light source, in particular for controlling it, and/or by at least one controlled mirror arranged in the beam path and/or by a layer, which is arranged in the beam path and is controllable with respect to its transparency.

In addition, the device has a system 105 for emitting an electromagnetic measuring beam 112, in particular a measuring light beam, which is reflected, preferably totally reflected, at the interface GF between the material 101 and the optical medium 108.

A detection device 106 is used for the detection of the reflected measuring beam 112, which forms a time-dependent response signal SR; the amplitude of the response signal SR is influenced by the wavelength of the excitation light SA and the intensity modulation of the excitation light SA, as will be explained in more detail below by means of examples.

The amplitude of the measuring signal depends on the wavelength of the excitation beam, the absorption properties of the sample and the thermal properties, in particular the thermal diffusivity and thermal conductivity of the sample and of the optical element. In addition, the coupling of the thermal signal from the sample into the optical element also plays a role.

A device 107 for analysing the material evaluates the detected response signals SR and in one embodiment generates a glucose or blood sugar level indication BZA.

Hereafter, the operation of the device 10 in accordance with FIG. 1 and in this connection, an example of a method for analysing a material 101 will be described in more detail for the case in which the material 101 to be analysed is human or animal tissue, and as part of the analysis of the material a glucose or blood sugar level indication BZA is to be determined.

With the device 105 an electromagnetic measurement beam 112, which is preferably a light beam in the visible wavelength range or an infrared light beam, is irradiated into the optical medium 108; this measurement beam 112 impinges on the interface GF below the first region 102 of the surface of the tissue. At the interface GF the measuring beam 112 is reflected and reaches the detection device 106, which measures the reflected measurement beam 112.

At the same time, one or more excitation beams SA, which are preferably infrared beams, are generated with the excitation light source 100. The wavelength of the infrared beams is preferably in a range between 3 μm and 20 μm, particularly preferably in a range between 8 μm and 11 μm.

The excitation beams SA are intensity- or amplitude-modulated with the device 104 for intensity modulation. In one embodiment short light pulses are generated with the device 104 for intensity modulation, preferably with a pulse frequency of between 1 kHz and 1 MHz, or else pulse packets (double or multiple modulation), preferably with envelope frequencies of 1-10 kHz.

The modulated excitation beams SA are coupled into the optical medium 108 and after passing through the interface GF arrive in the volume 103 within the tissue.

The wavelength of the excitation beams SA—with a view to the example of blood glucose measurement explained here—is preferably chosen such that the excitation beams SA are significantly absorbed by glucose or blood sugar. For measuring glucose or blood sugar the following infrared wavelengths are particularly well suited (vacuum wavelengths): 8.1 μm, 8.3 μm, 8.5 μm, 8.8 μm, 9.2 μm, 9.4 μm and 9.7 μm. In addition, glucose-tolerant wavelengths can be used, which are not absorbed by glucose, in order to identify other substances present and allow for excluding their effect on the measurement.

Due to the absorption of the excitation beams SA in the tissue in the region of the volume 103, a local temperature increase is induced, which triggers a heat transfer and thereby pressure waves in the direction of the interface GF; due to the resulting temperature and pressure fluctuations at the interface GF, the refractive index and/or the deformation, microstructure and the reflection behaviour are modulated in the region 102 and/or in the reflection region of the interface GF, and the beam path of the measuring beams 112 is affected.

If it is assumed, for example, that without excitation beams SA the alignment between the system 105 and the detection device 106 is optimal and a maximum received power is detected by the detection device 106, then due to the absorption of the excitation beams SA in the region of the volume 103 and due to the heat transport and the pressure waves, an (at least temporary) change in the amplitude or, in the case of a periodic modulation, the phase of the reflected measuring beam 112 can be induced, or an intensity modulation of the reflected measurement beam 112 can occur. The extent of the intensity modulation depends on the wavelength of the excitation beams SA (because of the necessary absorption in the tissue) and on the pulse frequency of the excitation beams SA (due to the temperature transport and the pressure waves from the tissue interior in the direction of the interface GF) and on the thermal properties of the sample and the medium.

The change in the reflection of the measuring beam 112 and/or the time-dependent change in the response signal SR is quantitatively acquired by the detection device 106, and the detection result D reaches the device 107.

On the basis of previously carried out calibration or comparison measurements, which in one embodiment are stored in a memory 107a of the device 107 in the form of comparison tables or comparison curves, the current concentration of glucose or blood sugar within the tissue or within the volume 103 can be deduced and a corresponding glucose or blood sugar indication BZA can be produced. The comparison tables or comparison curves may have been created, for example on the basis of glucose or blood sugar levels which were determined based on blood samples.

Particularly preferred embodiments and variants of devices 10 for analysing a material 101 are described below with reference to FIGS. 2 to 10.

The excitation transmission device 100 for emitting the excitation light beam or beams can be designed as an array, as shown in FIG. 2. The array has at least 5, advantageously at least 10, more advantageously at least 15 or at least 50 or 100 individually controllable emitters 100a for monochromatic light in the absorption spectrum of a material to be analysed.

The array preferably generates beams with monochromatic light with one or more, particularly preferably all of the following wavelengths (vacuum wavelengths): 8.1 µm, 8.3 µm, 8.5 µm, 8.8 µm, 9.2 µm, 9.4 µm and 9.7 µm and if desired, in addition glucose-tolerant wavelengths.

The device 105 for emission of the measuring light beam 112 and the detection device 106 can be arranged separately from the optical medium 108, as shown in FIG. 1. With a view to a minimal space requirement and minimal installation effort, it is regarded as advantageous if the device 105 for the emission of the measuring light beam 112 and the detection device 106 108 are mounted directly on the optical medium, preferably on opposite surface sections 108a and 108b of the optical medium 108, as FIG. 3 shows.

It can be provided that the excitation device/excitation light source 100 is permanently mechanically connected to the optical medium 108 either directly or by means of an adjustment device 109. The adjustment device 109 preferably allows an adjustment of the distance of the excitation light source 100 from the optical medium 108, and/or an adjustment in the beam longitudinal direction and/or an adjustment in a plane perpendicular thereto (see FIG. 4).

As shown in FIGS. 3, 4, 6, 7 and 8, the device 105 can be provided for emission of the measuring light beam 112 into the region of the optical medium 108 that is in contact with the first region 102 of the material surface. Such an arrangement allows the measuring light beam 112 to be irradiated at a flat angle and a total internal reflection to be induced at the interface of the optical medium 108 with the material 101.

By injecting the radiation at a flat (small) angle (to the sample surface), the mirage deflection, analogously to the known photothermal 'Bouncing Method', can be made more effective and at the same time the deformation-induced deflection of the measuring beam can be reduced. The angle between the sample surface and the measuring beam in one embodiment can be selected to be less than 20 degrees, less than 10 degrees, in particular less than 5 degrees, more particularly less than 2 degrees or 1 degree, in order to exploit this effect.

Conversely, by providing the irradiation at steeper (larger) angles (to the material surface), by analogy to the known photothermal 'Bouncing Method' the deflection can be made more effective and at the same time the mirage-effect related deflection of the measuring beam can be reduced. The angle between the material surface and the measuring beam in one embodiment can be selected to be greater than 20 degrees, greater than 30 degrees, in particular greater than 45 degrees, more particularly greater than 60 degrees or 70 degrees, to exploit this effect.

See related literature:

M. Bertolotti, G. L. Liakhou, R. Li Voti, S. Paolino, and C. Sibilia. Analysis of the photothermal deflection technique in the surface refection theme: Theory and Experiment. Journal of Applied Physics 83, 966 (1998)

The device 105 for emitting the measuring light beam 112 and/or the detection device 106 for detecting the measuring light beam 112 and/or the response signal SR, can be mechanically connected to the optical medium 108 in a supportive manner either directly or by means of an adjustment device, and/or coupled thereto by means of one or more fibre-optic cables 120.

Figure 6:
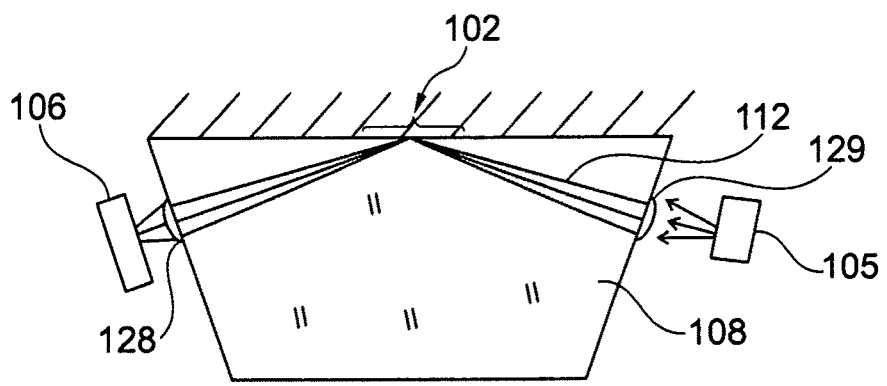

It can also be provided, as shown in FIG. 6, that the optical medium 108 directly supports an imaging optics 128 and/or an imaging optics 129 (in each case) in the form of a lens or other reflection or refraction means, and/or that an imaging optics is integrated into the optical medium 108. The imaging optics can, however also be integrated into the excitation transmission device or the device for generating the measuring beam, for example, in the form of a lens or other reflection or diffraction element, if these are designed as integrated components and/or as a semiconductor component. The imaging optics can in one embodiment be subtractively formed from the same semiconductor element by etching as the respective integrated circuit, which has a radiation source for the excitation or measuring beam.

Figure 7:
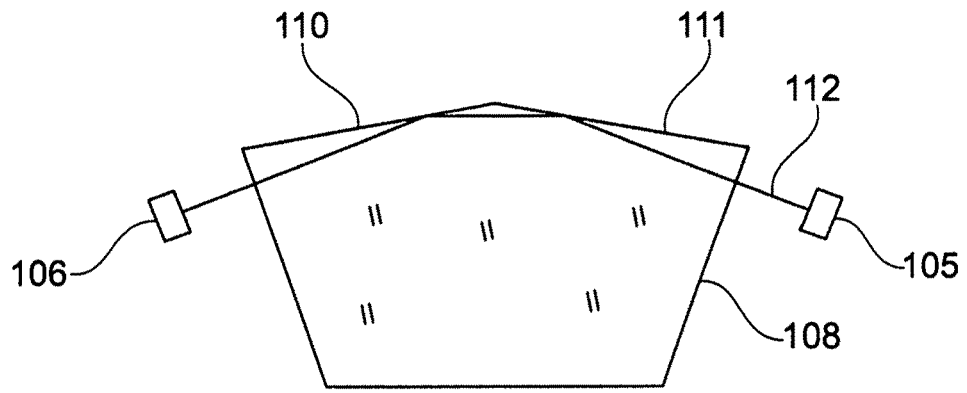

It can also be provided, as shown in FIG. 7, that the surface of the optical medium 108 has a plurality of partial faces 110, 111 inclined towards each other, at which the measuring light beam 112, is reflected or refracted multiple times.

It can also be provided, as shown in FIG. 3, that in or on the optical medium 108 one or more mirror surfaces 113, 114 are provided for reflecting the measuring light beam 112 (and therefore the response signal SR.) These mirror surfaces can be formed by inhomogeneities within the optical medium 108 or by its outer surfaces or by means of, for example, metallic or metallic coated mirror elements that are integrated/fitted/cast-in or mounted on the optical medium. This extends the optical path of the measuring light beam 112 in the optical medium 108 until its entry into the detection device 106, so that in the case of reflection at the region of the surface of the medium 108, which is in contact with the first region 102 of the material surface, a response signal-dependent deflection of the measuring light beam 112 within the optical medium 108 is increased. The deflection can then be detected in the detection device 106 as an absolute deflection.

The detection device 106 can have a plurality of optically sensitive surfaces, such as optically sensitive semiconductor diodes, or else a plurality of staggered openings 116, 117, 118 in a connector body 119 (FIG. 5), at which individual fibre-optic cables 120 end (FIG. 4), into which the light of the measuring light beam 112 is coupled depending on its deflection. The fibre-optic cables 120 are then connected to a connector body 119, which can be fixed to the optical medium 108, and direct the light to the part of the detection device 106 arranged at the end of the fibre-optic cable 120 (FIG. 4). The connector body 119 is then, in the same way as the fibre-optic cable 120, also part of the detection device 106 for detecting the measuring light beam.

For the sake of completeness, it should be noted that the excitation transmission device can also send the excitation to the material surface either as a whole or section by section by means of one or more fibre-optic cables, and in one embodiment the excitation transmission device can be directly coupled to one or more fibre-optic cables, which are coupled to the optical medium.

Figure 8:
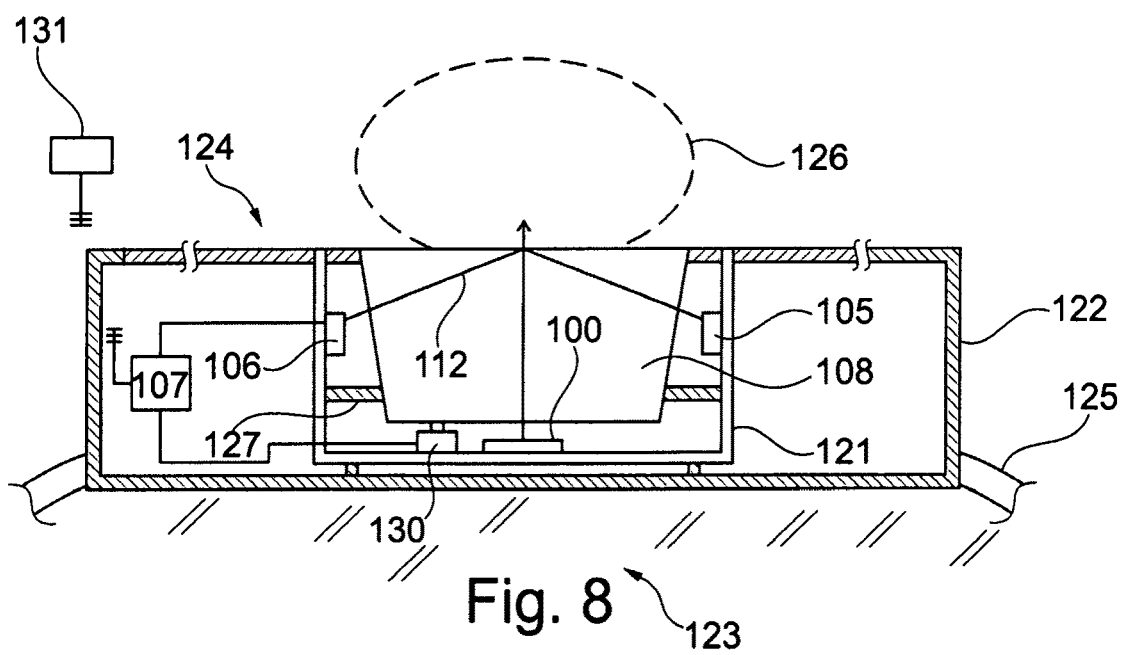

It can also be provided, as shown in FIG. 8, that the excitation transmission device 100, the device 105 for emitting the measuring light beam 112, and the detection device 106 are directly attached to each other or to a common support 121. The support can be formed by a plastic part, a printed circuit board or a metal sheet, which is mounted in a housing 122. The support, which in FIG. 8 is formed with a U-shaped cross section, can then at least partially surround the optical medium 108 in one embodiment. The optical medium can be attached to the support and adjusted relative to it.

The support can also be formed by the housing 122 itself or a housing part.

It can also be provided that the device with the housing 122 can be fastened to the body 123 of a person, wherein the excitation transmission device 100 for emitting one or more excitation light beams SA, the device 105 for emitting the measuring light beam 112 and the detection device 106 for detecting the time-dependent response signal SR are arranged and configured in such a way that the side that is suitable for performing the measurement (with a measuring window transparent to the excitation radiation) of the device is located on the side of the device facing away from the body, so that the material to be analysed can be measured on the side 124 of the housing 122 facing away from the body 123. In relation to this, FIG. 8 shows that the housing 122 is attached to the body 123 of a person by means of a belt 125 belonging to the housing 123, in one embodiment being in the form of a bracelet on a wrist. On the opposite side 124 from the wrist, the housing then has a window which is transparent to the excitation light beam SA, or the optical medium 108 is fitted directly into the outwards facing side 124 of the housing and itself forms the surface of some sections of the housing.

As shown in FIG. 8, a fingertip 126 shown schematically by a dashed line can then be placed on the optical medium 108 and measured.

The optical medium 108 can be attached within the housing 122, in the same way as the support 121, or else directly attached to the housing 122. The optical medium 108 can also be directly connected to the support 121, wherein an adjustment device 127 should be provided for the relative positioning of the support 121 with respect to the optical medium.

It is also conceivable to attach the excitation light source 100, the device 105 and the detection device 106, or even just one or two of these elements, directly to the optical medium 108 and the other element or elements to the support 121.

Through the optical window in the housing 122 and/or through the optical medium 108, other parameters of the material surface or the positioned fingertip 126 can be measured, such as in one embodiment, a fingerprint. For this purpose, in the housing an optical detector 130 in the form of a camera, for example, can be fastened to the support 121, which records a digital image of the material surface through the optical medium 108. This image is processed within a processing unit 107, which can be directly connected to the detection device and also to the excitation transmission device, in the same way as the measurement information by the detection device 106. The processing device can also perform control tasks for the measurement. It can also be at least partially separated and remote from the remaining parts of the device and communicate with these by means of a wireless connection.

The image data from the camera 130 can thus be further processed inside the housing, or via a radio link even outside the housing, and compared with a personal identity database to retrieve calibration data of the identified person.

This type of calibration data can also be stored for remote retrieval in a database, in one embodiment, a cloud. The measurement data from the detection device 106 can also be further processed both within and outside of the housing.

If data are processed outside the housing, then the resulting data should preferably be sent back to the device within the housing by radio to be displayed there.

In either case, a display can be provided on the housing 122, which advantageously can be read through the optical window, and in one embodiment also to some extent through the optical medium. The display can also project an optical indicator through the optical window onto a display surface and can have a projection device for this purpose. The display can be used in one embodiment to display a measurement or analysis result, in particular a glucose concentration. The information can be output in one embodiment via a symbolic or colour code. By means of the display or a signalling device parallel thereto, in one embodiment a proposal for an insulin dose can be presented, dependent on other patient parameters (e.g. insulin correction factor), or a signal can be transmitted automatically to a dosing device in the form of an insulin pump.

The connection of the device to and from an external data processing device 131 can be implemented using all common standards, such as fibre-optic cables, cable, wireless (e.g. Bluetooth, WiFi), or else ultrasound or infrared signals.

Figure 9:
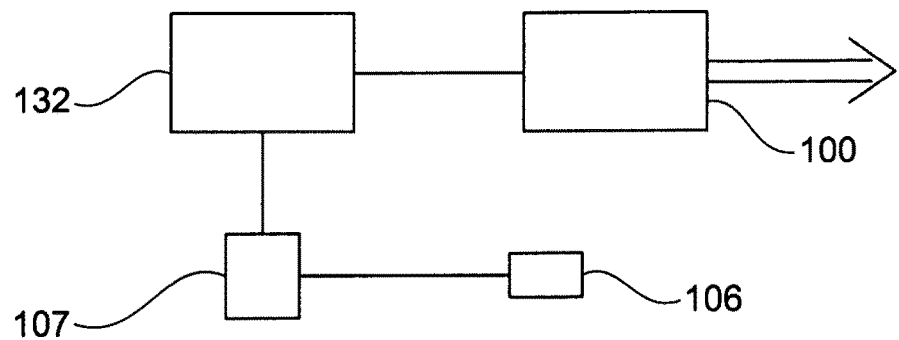

FIG. 9 shows a modulation device with a controller 132, which activates the excitation transmission device in a modulated manner. Both the controller 132 and the detection device 106 for the measuring light beam are connected to the evaluation device 107.

Figure 10:
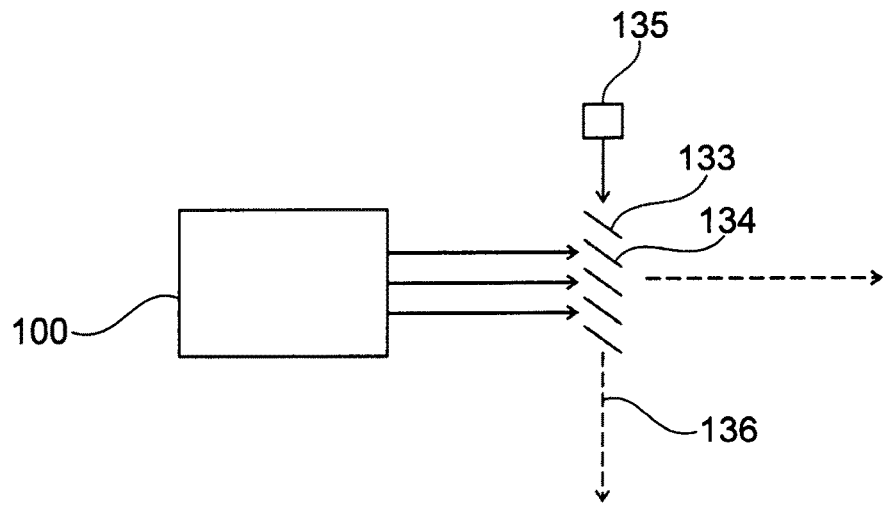

FIG. 10 shows an excitation light source 100, in front of which a mirror device driven by a MEMS (micro-electromechanical system) 135 is arranged, with one or more micro-mirrors 133, 134, such as those known from optical image projector technology, for the occasional deflection of the excitation light beam in a deflection direction 136.

Figure 11:
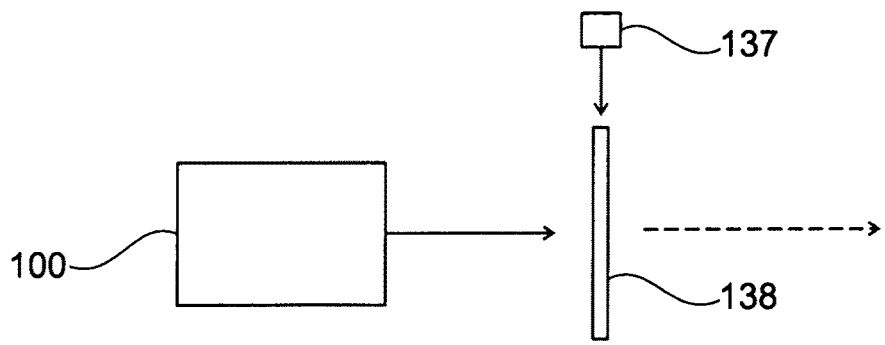

FIG. 11 shows an excitation light source 100, in front of which an optical layer 138 with a transmission that can be controlled by means of a control device 137 is arranged in the excitation light beam, in one embodiment with LCD cells.

The present property rights application (as already mentioned), in addition to the subject matter of the claims and exemplary embodiments described above, also relates to the following aspects. These aspects can be combined individually or in groups, in each case with features of the claims. Furthermore, these aspects, whether taken alone or combined with each other or with the subject matter of the claims, represent stand-alone inventions. The applicant reserves the right to make these inventions the subject matter of claims at a later date. This can be done either in the context of this application or else in the context of subsequent divisional applications or continuation applications claiming the priority of this application.

1) A method for analysing a material in a body, comprising:
emitting an excitation light beam with one or a plurality of specific excitation wavelengths through a first region of the surface of the body,
intensity modulating the excitation light beam with one or a plurality of frequencies, in particular consecutively, by means of a component which differs from a mechanical chopper, in particular by an electronic activation of the excitation light source, an adjustment device for a resonator of an excitation laser used as the excitation light source, or a movable mirror device, a controllable diffraction device, a shutter or mirror device which is coupled to a motor, such as a stepper motor, or to an MEMS, or a layer in the beam path that can be controlled in terms of its transmission,
by means of a detector positioned outside the body, detecting a response signal in a time-resolved manner, which response signal is attributable to the effect of the wavelength-dependent absorption of the excitation light beam in the body.

In one embodiment the modulation can be performed by interference or by influencing the phase or polarization of the radiation of the excitation transmission device, in particular if it comprises a laser light device.

2) The method according to aspect 1, characterized in that the excitation light beam is generated by a plurality of emitters or multi-emitters, in particular in the form of a laser array, which emit light with different wavelengths either simultaneously or sequentially, or in arbitrary pulse patterns.

3) The method according to aspect 1 or 2, characterized in that on the first region of the surface of the body an acoustic response signal is detected by an acoustic sensor.

4) The method according to any of the aspects 1 to 3, characterized in that a response signal is detected on the first region of the surface of the body by means of an infrared radiation sensor, in particular a thermocouple, a bolometer or a semiconductor detector, for example a quantum cascade detector.

5) The method according to any of the aspects 1 to 4, comprising the steps of:
producing the contact of an optical medium with a material surface, so that at least one region of the surface of the optical medium is in contact with the first region of the surface of the body;
emitting an excitation light beam with an excitation wavelength into a volume in the material located underneath the first region of the surface, in particular through the region of the surface of the optical medium which is in contact with the first region of the material surface,
measuring the temperature in the first region of the surface of the optical medium using an optical pyrometric method,
analysing the material on the basis of the detected temperature increase as a function of the wavelength of the excitation light beam.

6) The method according to aspect 5, characterized by emitting a measurement light beam through the optical medium (10) onto the region of the surface (12) of the optical medium (10) which is in direct contact with the material surface, in such a way that the measurement light beam and the excitation light beam overlap at the interface of the optical medium (10) and the material surface, at which the measurement light beam is reflected;
directly or indirectly detecting a deflection of the reflected measurement light beam as a function of the wavelength of the excitation light beam; and
analysing the material on the basis of the detected deflection of the measurement light beam as a function of the wavelength of the excitation light beam.

7) The method according to one of the aspects 5 or 6, characterized in that the measuring beam is generated by the same light source that generates the excitation light beam.

8) The method according to any one of aspects 5, 6 or 7, characterized in that after the deflection and before the detection within the optical medium, the measuring beam is reflected one or more times outside of the optical medium or partially inside and partially outside of the optical medium.

9) The method according to aspect 1 or any one of the other preceding or following aspects, characterized in that the measuring light beam is an intensity-modulated, in particular pulsed excitation light beam in particular in the infrared spectral range, wherein in particular the modulation rate is between 1 Hz and 10 kHz, preferably between 10 Hz and 3000 Hz.

10) The method according to aspect 1 or any one of the other preceding or following aspects, characterized in that the light of the excitation light beam/beams is generated by an integrated arrangement with a plurality of individual lasers, in particular a laser array, simultaneously or successively or partially simultaneously and partially successively.

11) The method according to aspect 1 or any one of the other preceding or following aspects, characterized in that from the response signals obtained at different modulation frequencies of the excitation light beam, an intensity distribution of the response signals is determined as a function of the depth below the surface in which the response signals are produced.

12) The method according to aspect 1 or any one of the other preceding or following aspects, characterized in that from the phase position of the response signals in relation to a modulated excitation light beam at one or different modulation frequencies of the excitation light beam, an intensity distribution of the response signals is determined as a function of the depth below the surface in which the response signals are produced.

13) The method according to aspect 11 or 12, characterized in that in order to determine the intensity distribution of the response signals as a function of the depth below the surface, the measurement results at different modulation frequencies are weighted and combined with each other.

14) The method according to aspect 11, 12 or 13, characterized in that from the intensity distribution obtained over the depth below the surface of the body, a material density of a material is determined, which absorbs the excitation light beam in specific wavelength ranges in a specific depth or depth range.

15) The method according to aspect 1 or any one of the other preceding or following aspects, characterized in that immediately before or after or during the detection of the response signal/signals at least one biometric measurement is carried out on the body in the first region of the surface or directly adjacent to this, in particular a measurement of a fingerprint, and the body, in particular a person, is identified and in that in particular, reference values (calibration values) can be assigned to the detection of the response signals.

16) A device for analysing a material, having a device for emitting one or more excitation light beams, each with one excitation wavelength, into a volume which is located in the material below a first region of its surface, with a device for modulating an excitation light beam, which device is formed by a modulation device of the radiation source, in particular its controller, an interference device, a phase- or polarization-modulation device and/or at least one controlled mirror arranged in the beam path, and/or a layer arranged in the beam path which is controllable with respect to its transparency, and having a detection device for detecting a time-dependent response signal as a function of the wavelength of the excitation light and the intensity modulation of the excitation light, and with a device for analysing the material on the basis of the detected response signals.

17) The device according to aspect 16, with a device for determining response signals separately according to different intensity modulation frequencies and/or with a device for determining response signals as a function of the phase position of the respective response signal relative to the phase of the modulation of the excitation light beam, in particular as a function of the modulation frequency of the excitation light beam.

18) The device for analysing a material according to aspect 16 or 17, with an optical medium for establishing the contact of the surface of the optical medium with a first region of the material surface, and with
a device for emitting an excitation light beam with one or more excitation wavelengths into a volume located in the material underneath the first region of the surface, in particular through the region of the surface of the optical medium which is in contact with the material surface, and with a device for measuring the temperature in the region of the surface of the optical medium which is in contact with the material surface using an optical method, and with a device for analysing the material on the basis of the detected temperature increase as a function of the wavelength of the excitation light beam and the intensity modulation of the excitation light beam.

19) The device according to aspect 18, characterized in that the excitation light source is directly fixedly mechanically connected to the optical medium.

20) The device according to aspect 18, characterized in that a device is provided for emitting a measurement light beam into the region of the optical medium which is in contact with the first region of the material surface, and that in order to detect the measurement light beam this device and/or the detection device is directly fixedly mechanically connected to the optical medium and/or coupled thereto by means of a fibre-optic cable.

21) The device according to aspect 18, 19 or 20, characterized in that the optical medium directly supports an imaging optics and/or that an imaging optics is integrated into the optical medium.

22) The device according to aspect 18 or any of the other preceding or following aspects, characterized in that the surface of the optical medium has a plurality of partial faces inclined towards each other, at which the measuring light beam is reflected multiple times.

23) The device according to aspect 18 or any of the other preceding or following aspects, characterized in that one or more mirror surfaces are provided in or on the optical medium for reflection of the measuring light beam.

24) The device according to aspect 16 or 17, characterized in that in order to detect a time-dependent response signal, the detection device has an acoustic detector for detecting acoustic waves on the material surface, in particular with a resonator, more particularly with a Helmholtz resonator. As the detector of the acoustic source a quartz fork is used, preferably with the same resonance frequency as the resonator. The resonator can be open or closed. The quartz fork is preferably in or on the neck of the resonator (off-beam) or inside or outside of the resonator (in-beam).

25) The device according to aspect 16, 17 or 18, characterized in that in order to detect a time-dependent response signal, the detection device has a thermal radiation detector for detecting the heat radiation at the material surface, in particular an infrared detector, more particularly a thermocouple, a bolometer, or a semiconductor detector.

26) The device according to any one of the aspects 16 to 25, characterized in that the excitation light source and the detection device are directly attached to each other or to a common support, which is formed in particular by a housing or housing part of the device.

27) The device according to any one of the aspects 16 to 26, characterized in that the device has a wearable housing which can be fastened to the body of a person, wherein the device for emitting one or more excitation light beams and the detection device for detecting a time-dependent response signal are arranged and configured in such a way that the material to be analysed is measured on the side of the housing facing away from the body.

28) The device according to any one of the aspects 16 to 26, characterised in that the device has a wearable housing, which can be fastened to the body of a person, and that the housing of the device has a window which is transparent for the excitation light beam on its side facing away from the body in the intended wearing position.

29. A device for analysing a material with an excitation transmission device for generating at least one electromagnetic excitation beam, in particular an excitation light beam, with at least one excitation wavelength, a detection device for detecting a response signal and a device for analysing the material on the basis of the detected response signal.

30. The device according to any one of the preceding aspects 16 to 29, characterized in that the detection device is configured for measuring the deformation of a crystal.

The deformation can be measured more effectively by analogy with the photothermal 'Bouncing method' by the selection of steeper (larger) angles of incidence of the measuring beam to the sample surface and the influence of the mirage effect-related deflection of the measuring beam can be minimized.

Literature

M. Bertolotti, G. L. Liakhou, R. Li Voti, S. Paolino, and C. Sibilia. Analysis of the photothermal deflection technique win the surface refection theme: Theory and Experiment. Journal of Applied Physics 83, 966 (1998)

A cantilever can be placed either directly on the sample or on a sufficiently thin optical medium, on which the sample is placed on the one side and the cantilever on the opposite side. Due to the thermal expansion of the sample or the optical element, the cantilever is set into vibration by the thermal expansion caused by the absorption of the modulated pumped beam. The measuring beam is reflected onto the upper side of the tip of the cantilever and is deflected due to the vibration, by an amount depending on the irradiated wavelength and the thermal properties of the sample, and on the modulation frequency. This deflection is detected.

31. The device according to any one of the preceding aspects 16 to 30, characterized in that the excitation transmission device contains an interrogation laser or an LED, for example an NIR (near-infrared) LED.

32. The device according to any one of the preceding aspects 16 to 31, characterized in that the excitation transmission device comprises a probe laser, which has a smaller diameter than an additional pump laser.

33. The device according to any one of the preceding aspects 16 to 32, characterized in that in order to achieve a more favourable signal-to-noise ratio, a special coating, in particular of the optical emitter, for example IRE is provided, so that heat is dissipated better (e.g. "thermal conducting paste").

The optical element can be coated on the contact surface in such a way that an improved conduction of the thermal signal into the optical medium can be provided. In addition, the coating can also serve as protection against scratches, and by intelligent choice of material can also implement a reflective surface for the measuring beam. In this case, the transparency for the excitation light must be maintained.

34. The device according to any one of the preceding aspects 16 to 33, characterized in that the device has a system for
   i. pulse trains/double modulation
   ii. oscillating mirror
   iii. MEMS interferometer.

35. The device according to any one of the preceding aspects 16 to 34, characterized in that the device is designed to be permanently wearable by a person on the body, in one embodiment by means of a retaining device connected to the housing, such as a belt, a band or a chain or a clasp, and/or in that the detection device has a detection surface, which can also be used as a display surface for information such as measurement values, clock times and/or textual information.

36. The device according to the preceding aspect 35, characterized in that the device has a pull-off film in the area of the detection surface, preferably next to the detection surface, for the pre-treatment of the material surface and for ensuring a clean surface and/or which in one embodiment in the case of glucose measurement, is specifically provided for the purpose of skin cleansing.

37. The device according to any one of the preceding aspects 16 to 36, characterized in that the detection device is configured to read and recognize fingerprints to retrieve certain values/calibrations of a person and/or to detect the location of a finger, preferably to detect and determine an unintended movement during the measurement.

38. The device according to any one of the preceding aspects 16 to 37, characterized in that the detection device has a results display, which is implemented, preferably with colour coding, as an analogue display, in one embodiment including an error indication (for example: "100 mg/dl plus/minus 5 mg/dl"), acoustically and/or with a result display of measurements in larger steps than the accuracy of the device allows. This means that, for example, small fluctuations which could unsettle a user are not communicated.

39. The device according to any one of the preceding aspects 16 to 38, characterized in that the device comprises data interfaces for the transfer of measured data and the retrieval of calibration data or other data from other devices or cloud systems, wherein the device is preferably configured in such a way that the data can be transmitted in encrypted form, in particular can be encrypted by fingerprint or other biometric data of the operator.

40. The device according to any one of the preceding aspects 16 to 39, characterised in that the device is configured in such a way that a proposed insulin dose to be given to a person can be determined by the device in conjunction with other data (e.g. insulin correction factor) and/or weight, body fat can be measured and/or manually specified at the same time or can be transmitted from other devices to the device.

41. The device according to any one of the preceding aspects 16 to 40, characterized in that in order to increase the measurement accuracy, the device is configured to identify further parameters, in one embodiment using sensors for determining the skin temperature, diffusivity, conductivity/moisture level of the skin, for measuring the polarization of the light (secretion of water/sweat on the finger surface) or such like.

Water and sweat on the skin surface of a person, which can influence the glucose measurement, can be detected by a test stimulus with an excitation radiation using the excitation transmission device with the water-specific bands at 1640 cm-1 (6.1 μm) and 690 cm-1 (15 μm). If the absorption should exceed a certain value, the measurement site/material surface/skin surface is too wet for a reliable measurement. Alternatively, the conductivity of the substance in the vicinity or directly at the measurement site can be measured, in order to determine the moisture level. An error message and an instruction to dry the surface can then be output.

42. The device according to any one of the preceding aspects 16 to 41, characterized in that the device has a cover in the beam path of the pumping and/or measuring beam laser. This ensures the compulsory eye safety for human beings is provided.

43. The device according to any one of the preceding aspects 16 to 42, characterized in that the device has a replaceable detection surface.

44. The device according to any one of the preceding aspects 16 to 43, characterized in that the device is provided in some areas with a grooved or roughened crystal as an optical medium, which allows a better adjustment of the sample (e.g. the finger). The measuring point, on which the surface of the material to be analysed is placed, is preferably designed without grooves and smooth.

45. The device according to any one of the preceding aspects 16 to 44, characterised in that for the measuring beam either a cylindrical TEMpl TEM00 mode can be used, or other modes can be used instead of the cylindrical TEMpl TEM00 mode, e.g. TEM01 (Doughnut), TEM02 or TEM03. Particularly the latter modes have the advantage that their intensity can be matched to the sensitivity profile of the quadrant diode, which forms the detector for the deflected measuring beam (see figures). In addition, rectangular modes TEMmn can be used, such as TEM30 or TEM03 or higher. This allows sampling/measuring beams to be used which are less prone to interference in the horizontal or vertical direction.

46. The device according to any one of the preceding aspects 16 to 45, characterised in that the device measures not only at a point but in a grid. This can be done either by displacing the pumped or probe laser or the detection unit. Instead of a displacement, one or more arrays of pumping or probe lasers are possible.

Other detection methods for the detection of a response signal after emission of an excitation beam may comprise:
photo-acoustic detection—photo-acoustic detection using a tuning fork or other vibration element or: a slightly modified form of photo-acoustics with an open QePAS cell (Quartz-enhanced Photo-Acoustic Spectroscopy). These methods can be used to detect pressure fluctuations/vibrations on the surface and evaluate them in the manner described above for the measured beam deflection.

In principle, measured values of a phase shift of the response signal relative to a periodic modulation of the excitation beam can be used for depth profiling. (To this end, warming/cooling phases of the material surface should be more accurately evaluated with regard to their waveform or pattern.)

The device described can be associated with a supply of adhesive strips for removing dead skin layers, in order to allow a maximally undistorted measurement on a human body, as well as plasters with thermal conductive paste that can be applied to the optical medium on a regular basis. The optical medium can be replaceable, given suitable fastening and adjustment of the remaining parts.

To perform the measurement, the device can be provided and configured not only on a person's finger, but also on a lip or an earlobe.

In some embodiments the measurement can work even without direct contact and placement of the finger or other part of the body (at a distance), resulting in a contact-free measurement.

The measurement can be improved with regard to its accuracy and reliability by combination of a plurality of the measuring systems described and explained, with similar susceptibility to error.

DAQ and lock-in amplifiers in the evaluation can be combined in one device and overall the evaluation can be digitized.

The measuring device can also be performed on a moving surface, so that in the course of a grid measurement: excitation light source and and/or measuring light source move over the skin in a grid pattern during the measurement, which allows skin irregularities to be compensated for or even eliminated.

The sensitivity of the detection device/deflection unit can be optimized by adjustment/variation of the wavelength of the probe beam/measurement light source. For this purpose, the measurement light source can be varied with respect to wavelength or else contain a plurality of laser light sources at different wavelengths for selection or combination.

For the deflection of the pump/probe laser an ideal transverse mode (TEM) can be selected.

The excitation transmission device, measuring light source and detector can be configured as a common array and the beams can be suitably deflected in the optical medium to concentrate the emission and reception of all beams at one point.

A lens on or in the crystal of the optical medium can contribute to deflecting the measuring light beam more strongly depending on the response signal.

In addition, it is conceivable to use a gap-free photodiode for the detection, and a lens could then focus the measuring light beam after its exit, to thus enable a more accurate measurement.

Figure 12:
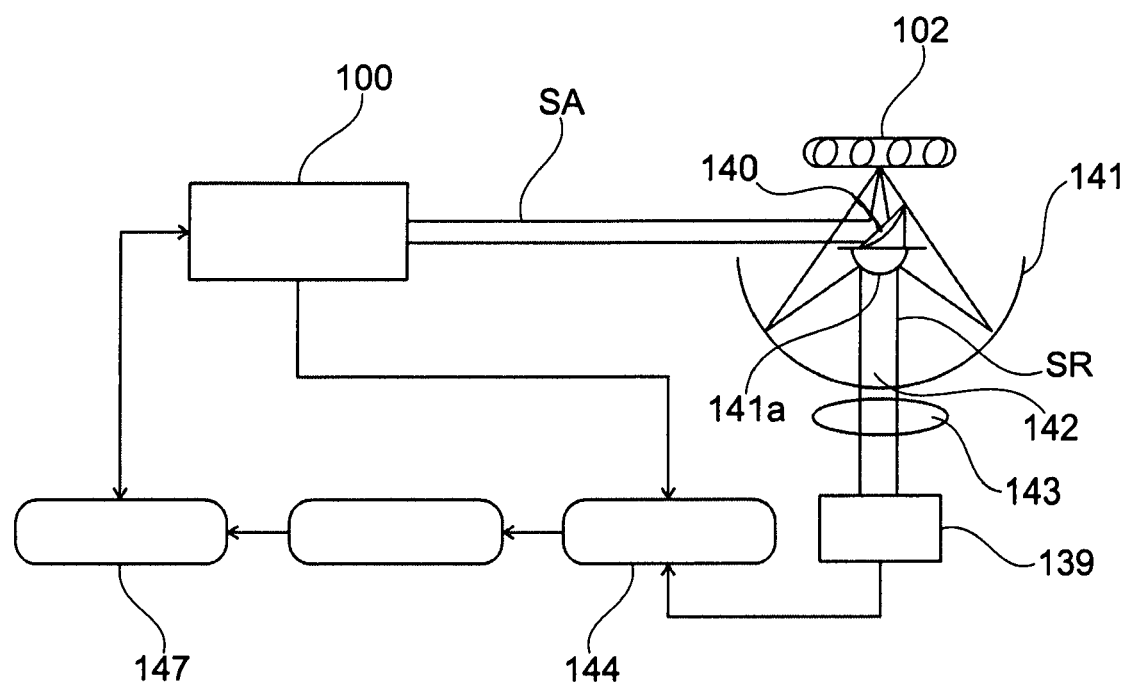
Figure 13:
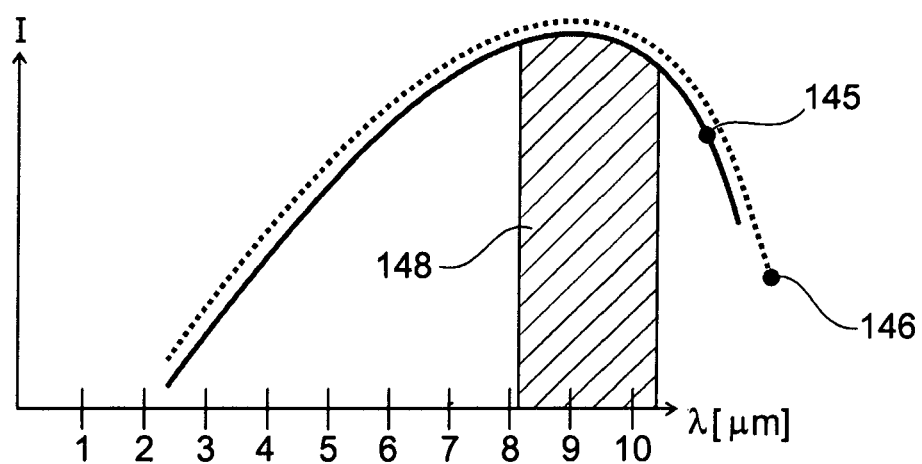

An additional variant of the invention, in accordance with the patent claims is described in the following concept. This concept, whether taken alone, in combination with the above aspects or with the subject matter of the claims, also constitutes at least one independent invention. The applicant reserves the right to make this invention or these inventions the subject of claims at a later date. This can be done either in the context of this application or else in the context of subsequent divisional applications or continuation applications claiming the priority of this application:

A concept for non-invasive blood sugar measurement by a determination of the glucose in the skin by means of excitation using quantum-cascade lasers and measurement of the thermal wave by radiant heat. On the basis of FIGS. 12 and 13 a method is described with which the concentration of the glucose or another material in the interstitial fluid (ISF) in the skin can be determined. Glucose in the ISF is representative of blood glucose and follows it rapidly in the event of changes. The method consists of at least individual steps or groups of the following steps or of the entire sequence:

1. The point on the skin 102 (in this case, the first region of the material surface), is irradiated with a beam of a quantum cascade laser, which is focused and possibly reflected at a mirror or parabolic mirror 140, and which is incrementally or continuously tuned over a specific infrared range, in which glucose is specifically absorbed. Instead of the quantum cascade laser 100, a laser array with a plurality of lasers radiating at single wavelengths can also be used. The spectral range (or the individual wavelengths, typically 5 or more wavelengths) can be in particular between approximately 900 and approximately 1300 $cm^{-1}$, in which glucose has an absorption fingerprint, that is to say, typical and representative absorption lines.

2. The excitation beam designated with SA is employed continuously (CW lasers) or in pulsed mode with a high pulse repetition rate or in a modulated manner. In addition, the excitation beam is low-frequency modulated, in particular in the frequency range between 10 and 1000 Hz. The low-frequency modulation can be performed with a variety of periodic functions, in various embodiments sine-wave, square wave or sawtooth wave, or the likes.

3. Due to the irradiation of the skin the IR-radiation penetrates the skin to a depth of roughly 50-100 μm and—depending on the wavelength—excites specific vibrations in the glucose molecule. These excitations from the vibration level v0 to v1 return to the initial state within a very short time; in this step heat is released.

4. As a result of the heat produced according to (3) a thermal wave is formed, which propagates isotropically from the place of absorption. Depending on the thermal diffusion length, defined by the low-frequency modulation described in (2) above, the thermal wave reaches the surface of the skin periodically at the modulation frequency.

5. The periodic emergence of the thermal wave at the surface corresponds to a periodic modulation of the thermal radiation property of the skin (material surface of the sample). The skin can be described here approximately as a black body radiator, whose entire emission according to the Stefan-Boltzmann law is proportional to the fourth power of the surface temperature.

6. With a detector 139 for heat radiation, i.e., an infrared detector, i.e. a thermocouple, bolometer, semiconductor detector or similar device, which is directed at the point of the skin under irradiation, the periodic temperature increase described under (5) is recorded. It depends on the irradiation of infrared light described under (1) and (2), and on the absorption described under (3), and therefore depends on the concentration of glucose. The thermal radiation SR (in this case, the response signal) is collected by means of an optical element, in one embodiment an infrared lens or a mirror, in particular a concave parabolic mirror 141, and, in one embodiment is directed via a convex mirror 141a on to the detector 139. For this purpose a collection mirror used in one embodiment can have an opening 142, through which the collected beam is directed. A filter 143 can also be provided in the beam path, which only allows infrared radiation of a certain wavelength range to pass.

7. In processing the response signals, the modulation frequency can be specifically taken into account, for which the response signal can be processed in a lock-in amplifier 144. By analysis of the phase angle between the excitation signal and heat radiation signal (response signal) using a control and processing unit 147, the depth information relating to the depth below the surface can be obtained, from which the response signals are largely obtained.

8. The depth information can also be obtained by the selection and analysis of various low-frequency modulation frequencies as described in (2) for the excitation beam and the combination of the results for different modulation frequencies (wherein the results can also be weighted differently for different modulation frequencies). Difference methods or other calculation methods can be used for this, to compensate for the absorption of the topmost skin layers.

9. To maximise the sensitivity in the detection of the thermal radiation according to point (6), it is used over a broad spectral band for the entire available infrared range. As many regions of the Planck radiation curve as possible should be used. To make the detection insensitive to the intensive excitation radiation, the detection of the heat radiation is provided with blocking filter (notch filter) 143 for these excitation wavelengths. The wavelength range 148 transmitted through the blocking filter 143 is also apparent from the diagram of FIG. 13. Therein, the intensity of the response signal is shown both as a function of the wavelength, in a first (solid) curve 145 without an excitation beam or only with excitation radiation in non-specific wavelengths for the material to be identified (i.e. without the wavelengths where specific absorption bands of the material exist), and then in a second (dashed) curve 146 a similar curve is shown, wherein an excitation beam is irradiated which contains specific absorption wavelengths of the material to be identified.

10. From the thermal signal measured according to (6-9), which is dependent on the excitation wavelength, if glucose is to be identified, in one embodiment the background is determined first with non-glucose-relevant wavelengths (or excluding them) of the excitation beam (curve 145), and then with (or including) the glucose-relevant wavelengths the difference from the background signal is determined. This results in the glucose concentration in the skin layer or skin layers, which are defined by the selected phase position according to (7) or the different modulation frequencies according to (8) or a combination of these.

Although the invention has been illustrated and described in greater detail by means of preferred exemplary embodiments, the invention is not limited by the examples disclosed and other variations can be derived therefrom by the person skilled in the art without departing from the scope of protection of the invention.

LIST OF REFERENCE NUMERALS 10 device
100 excitation transmission device/excitation light source
100a emitters/transmission elements
101 material
102 first region
103 volume
104 device
105 device
106 detection device
107 processing device/evaluation device
107a memory
108 optical medium
108a surface section
108b surface section
109 adjustment device
110 partial surface
111 partial surface
112 measuring beam/measuring light beam
113 mirror surface
114 mirror surface
116 opening
117 opening
118 opening
119 connector body
120 fibre-optic cable
121 support
122 housing
123 body
124 side
125 belt
126 fingertip
127 adjustment device
128 imaging optics
129 imaging optics
130 optical detector/camera
131 data processing device
132 controller
133 micro-mirror
134 micro-mirror
135 micro-electro-mechanical system
136 deflection device
137 control device
138 layer
139 infrared detector
140 mirror
141 parabolic mirror
142 opening in 141
143 wavelength filter
144 lock-in amplifier
145 signal curve of the response signal (solid line)
146 signal curve of the response signal (dashed line)
147 control and processing device
148 wavelength range
BZA blood sugar level indication
D detection result
GF interface
SA excitation beam
SR response signal

The invention claimed is:

1. A device for analysing human or animal tissue for non-invasive glucose or blood sugar measurement, said device having
    an excitation transmission device for generating at least one excitation light beam with at least one excitation wavelength and radiating the at least one excitation light beam into a tissue volume, which is located underneath a first region of a surface of the tissue,
    an optical medium, which in operation is in direct contact with said first region of the surface of the tissue,
    a detection device for detecting a response signal, which response signal is attributable to the effect of the wavelength-dependent absorption of the excitation light beam in the tissue,
    wherein detecting said response signal comprises one of detecting a measuring beam, after this measuring beam has been reflected at least once at an interface of the optical medium, which is in contact with the first region of the surface of the tissue, and detecting a deformation and/or density change of the optical medium using a piezo element connected to or integrated in said optical medium,
- a device for the intensity modulation of the excitation light beam, and
- a device for analysing the tissue on the basis of detected response signal, said device being configured for successively determining, using different modulation frequencies of the excitation light beam, response signals, and for combining results obtained with different modulation frequencies with each other and obtaining specific information for a depth range under the surface from this.

2. The device according to claim 1, wherein
the excitation transmission device is a radiation source, a monochromatic, in particular a polarised radiation source, more particularly a laser light source,
wherein the excitation transmission device is preferably arranged such that the emitted excitation beam penetrates the optical medium and exits the same again at a predetermined point on the surface of the optical medium, and
the device comprises a system for emitting a measurement beam, in particular a measurement light beam, which is arranged so that the emitted measurement beam penetrates the optical medium and wherein preferably in operation the measuring beam and the excitation beam overlap at an interface of the optical medium and the surface of the tissue, at which the measuring beam is reflected, and
the detection device is a device for receiving the reflected measuring beam which forms the response signal and/or for directly or indirectly detecting a deflection of the reflected measuring beam.

3. The device according to claim 1, wherein the device comprises an optical medium, which is in direct contact with the tissue, in particular with a first region of the surface of the tissue, and that in order to detect a response signal the detection device detects a parameter change of the optical medium, in particular in a region adjacent to the first region, as a result of the response signal, in particular a deformation and/or density change of the optical medium.

4. The device according to claim 1, wherein the detection device is suitable for detecting a time-dependent response signal as a function of the wavelength of the excitation light and/or the intensity modulation of the excitation light.

5. The device according to claim 1, wherein the excitation transmission device comprises two or more transmission elements, in particular in the form of a one-, two- or multi-dimensional transmission element array.

6. The device according to claim 1, wherein the excitation transmission device comprises two or more lasers, in particular in the form of a one-, two- or multi-dimensional laser array, and/or two or more light-emitting diodes, in particular in the form of a one-, two- or multi-dimensional diode array.

7. The device according to claim 1, wherein the excitation transmission device is directly, or indirectly by means of an adjustment device, mechanically fixedly connected to an optical medium which is in direct contact with the tissue, in particular with the first region of the surface of the tissue.

8. The device according to claim 1, wherein the device for emitting a measuring beam and the detection device are aligned with respect to each other in such a way that the detection device detects the measuring beam as the time-dependent response signal, after this beam has been reflected at least once at the interface of the optical medium, which is in contact with the tissue, in particular with the first region of the surface of the tissue.

9. The device according to claim 1, wherein the device for emitting a measuring beam and/or the detection device and/or the excitation transmission device are directly mechanically fixedly connected to the optical medium and/or coupled to the same by means of a fibre-optic cable.

10. The device according to claim 1, wherein the optical medium directly supports an imaging optics, and/or an imaging optics is integrated into the optical medium.

11. The device according to claim 1, wherein the excitation transmission device and/or the device for the emission of the measuring beam and/or the detection device are directly attached to each other or to a common support.

12. The device according to claim 1, wherein the excitation transmission device has an integrated semiconductor component, which comprises one or more laser elements and at least one micro-optical component and preferably an additional modulation element.

13. A method for analysing human or animal tissue for non-invasive measuring of glucose or blood sugar, wherein in the method
- an optical medium is brought into direct contact with a first region of the surface of the tissue,
- with an excitation transmission device, at least one electromagnetic excitation light beam with at least one excitation wavelength is generated by an at least partially simultaneous or consecutive operation of a plurality of laser emitters of a laser light source, wherein the intensity of said excitation light beam is modulated at a modulation frequency and said at least one excitation light beam is radiated into a tissue volume, which is located underneath said first region of a surface of the tissue,
- with a detection device a response signal is detected, which response signal is attributable to the effect of the wavelength-dependent absorption of the excitation light beam in the tissue, wherein detecting said response signal comprises one of detecting a measuring beam, after this measuring beam has been reflected at least once at an interface of the optical medium, which is in contact with the first region of the surface of the tissue, and detecting a deformation and/or density change of the optical medium using a piezo element connected to or integrated in said optical medium, and
- the tissue is analysed on the basis of the detected response signal, wherein said analysing the tissue on the basis of the detected response signal comprises successively determining, using different modulation frequencies of the excitation light beam, response signals, and combining results obtained with different modulation frequencies with each other and obtaining specific information for a depth range under the surface from this.

14. The method according to claim 13, wherein
the emitted excitation beam is radiated in such a way that it penetrates the optical medium and exits the same at a predetermined point on the surface of the optical medium, and
with a device for emitting said measuring beam, said measuring beam is generated in such a way that it penetrates the optical medium.

15. The method according to claim 13, wherein as a function of a glucose concentration identified in the tissue, a dosing device is activated for delivering a substance into the tissue, and/or an acoustic and/or visual signal is output and/or a signal is delivered to a processing device via a wireless connection.

16. The method according to claim 14, wherein in operation the measuring beam and the excitation beam overlap at an interface of the optical medium and the surface of the tissue, at which the measuring beam is reflected.

17. The method according to claim 13, wherein the deflection of the reflected measuring beam is directly or indirectly detected.

* * * * *